United States Patent [19]

Yamabe et al.

[11] 4,089,869

[45] May 16, 1978

[54] PROCESS FOR PRODUCING PERFLUOROLACTONE

[75] Inventors: Masaaki Yamabe, Machida; Seiji Munekata; Seisaku Kumai, both of Yokohama; Shunichi Samejima, Tokyo, all of Japan

[73] Assignee: Asahi Glass Company Ltd., Tokyo, Japan

[21] Appl. No.: 722,076

[22] Filed: Sep. 10, 1976

[30] Foreign Application Priority Data

Sep. 23, 1975 Japan ............................. 50-114333

[51] Int. Cl.$^2$ ............................................. C07D 307/32
[52] U.S. Cl. ............................. 260/343.5; 260/343.6; 260/343.9
[58] Field of Search ............. 260/343.5, 343.6, 343.9, 260/487

[56] References Cited

U.S. PATENT DOCUMENTS 3,346,594  10/1967  Merijan et al. ...................... 260/343

OTHER PUBLICATIONS

Pirkle, et al., J. Org. Chem. 1969, 34(8), 2239–2244.

Primary Examiner—Cecilia M. S. Jaisle
Attorney, Agent, or Firm—Oblon, Fisher, Spivak, McClelland & Maier

[57] ABSTRACT

A perfluorolactone having the formula

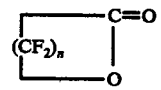

wherein $n$ is an integer of 2 to 4, is produced by reacting a fluoro compound having the formula

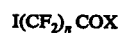

$I(CF_2)_n COX$ wherein $n$ is an integer of 2 to 4 and X represents a halogen atom, —OR or —NR$^1$R$^2$, and R, R$^1$ and R$^2$ respectively represent hydrogen atom or a C$_1$–C$_{10}$ alkyl group, with fuming sulfuric acid.

9 Claims, No Drawings

PROCESS FOR PRODUCING PERFLUOROLACTONE

BACKGROUND OF THE INVENTION

The present invention relates to a process for producing a perfluorolactone. More particularly, it relates to a process for producing a perfluorolactone having the formula

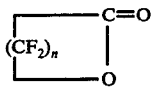

by reacting a fluoro compound having the formula $$I(CF_2)_nCOX$$

with fuming sulfuric acid.

The perfluorolactones are remarkably useful as intermediates for various fluorine-containing compounds or compounds having special characteristics. For example, the perfluorolactones can be easily converted to the corresponding perfluorodicarboxylic acid derivatives by reacting with a nucleophilic reagent.

These derivatives can be effectively used as polybasic acids for producing fluorine-containing condensation polymers such as polyamides or polyesters.

On the other hand, the perfluorolactones are intermediates useful for synthesis of various fluorine-containing vinyl monomers especially fluorine-containing vinyl ethers, and they impart excellent characteristics such as lubricants, fiber processing agents, etc..

Thus, these useful perfluorolactones have been hard to produce in high yield. Moreover, complicated processes have been required for producing them.

A satisfactory industrial process for producing them has not been known. For example, perfluoro- γ-butyrolactone has been produced by heating disilver perfluoroglutarate at 125° C in the presence of iodine by R. E. Banks et al.

However, the yield of the object compound of perfluoro- γ-butyrolactone was only 8% or less (JCS (C( 1967, 2333).

The inventors have found that perfluorolactones can be produced in high yield by reacting α,ω-diiodoperfluoroalkane having 3 to 5 of carbon atoms with fuming sulfuric acid.

However, when 1,4-diiodoperfluorobutane is used as starting material, the corresponding perfluorolactone can be obtained in about 50 to 60% of yield, and the reaction product usually contains 10 to 15% or more of perfluorodicarboxylic fluoride.

Since both compounds have similar boiling point, it is hard to obtain the perfluorolactone having high purity by separating them.

SUMMARY OF THE INVENTION

It is an object of the present invention to provide a process for producing perfluorolactone in high selectivity and high yield.

It is another object of the invention to provide a process for producing perfluorolactone in a yield of higher than 70% without incorporating the corresponding perfluorodicarboxylic fluoride.

These objects of the present invention have been attained by producing perfluorolactone having the formula

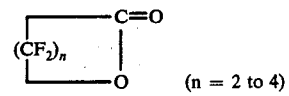

by reacting a fluoro compound having the formula $$I(CF_2)_nCOX$$

wherein $n$ is an integer of 2 to 4 and X represents a halogen atom, —OR or —NR$^1$R$^2$ and R, R$^1$ and R$^2$ respectively represent hydrogen atom or a C$_1$ - C$_{10}$ alkyl group with fuming sulfuric acid.

DETAILED DESCRIPTION OF THE PREFERRED EMBODIMENTS

In the process of the invention, it is important to use the fluoro compound having the formula $$I(CF_2)_nCOX$$

as the starting material.

Since I(CF$_2$)$_n$COX is used as starting material, the by-production of the isomer of the perfluorolactone i.e. the perfluorodicarboxylic fluoride is inhibited so as to obtain the perfluorolactone having high purity without incorporating the perfluorodicarboxylic fluoride.

The perfluorolactone can be obtained in remarkably high yield by reacting it with fuming sulfuric acid in comparison with the conventional process. In the formula $$I(CF_2)_nCOX,$$

$n$ is an integer of 2 to 4 and X represents —F, Cl, —Br, —I, —OR or —NR$^1$R$^2$ and R, R$^1$ and R$^2$ respectively represent hydrogen atom or a C$_1$ - C$_{10}$ alkyl group.

It is especially preferable to use the fluoro compound having the formula $$I(CF_2)_3COF$$

($n$ is 3 and X is fluorine atom), because of availability of the starting material. In the formula, R, R$^1$ and R$^2$ are preferably hydrogen atom or a C$_1$ - C$_3$ lower alkyl group.

The fluoro compounds having the formula which are used as the starting material in the process of the invention, can be easily obtained by a telomerization using a telogen of ICF$_2$COF, and a taxogen of CF$_2$ = CF$_2$ in the presence of a radical initiator such as benzoyl peroxide. The fluoro compounds having the formula I(CF$_2$)$_n$COF can be also obtained by the other methods.

The flouro compounds having the formula I(CF$_2$)$_n$COX wherein X is —OR or —NR$^1$R$^2$ can be obtained by reacting the compound having the formula I(CF$_2$)$_n$COF with the corresponding alcohol or amine. In accordance with the telomerization, the adducts of 1 mole of CF$_2$ = CF$_2$ are useful as I(CF$_2$)$_3$COX ($n$ = 3) which are separated from the reaction mixture in the telomerization by the conventional method.

In the conversion of I(CF$_2$)$_n$COX to the perfluorolactone in the invention, fuming sulfuric acid is preferably used.

The concentration of $SO_3$ in the fuming sulfuric acid is preferably in the range of about 5 to 95% by weight preferably 20 to 60% by weight.

A catalyst can be used if desired.

The catalysts can be mercuric sulfates, cadmium sulfate, zinc sulfate, antimonyl pentachloride, antimonyl dichlorotrifluoride, and antimonyl pentafluoride may also be used as catalysts.

A small amount of chlorine gas can be added, if desired.

The conditions of the reaction of the fluoro compound with the fuming sulfuric acid are not strictly limited and various operations and conditions can be employed. It is preferable to select the optimum operating condition under consideration of the kind of the starting materials, and the kind and boiling point of the object product of perfluorolactone.

The reaction temperature is higher than room temperature, usually in a range of about 30° to 150° C, preferably 50° to 130° C, especially in a range of about 60° to 110° C so as to smoothly perform the reaction. It is preferable to use 1 to 100 moles, preferably 2 to 20, especially 3 to 10 moles of the fuming sulfuric acid per 1 mole of the fluoro compound having the formula

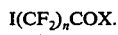

It is preferable to use excess of the fuming sulfuric acid to the fluoro compound such as more than 0.1 mole preferably more than 1.0 mole as the content of $SO_3$ in the fuming sulfuric acid per 1 mole of the fluoro compound. In the operation for the reaction, various methods can be employed such as a method of charging desired amount of the fluoro compound and the fuming sulfuric acid in a reactor and heating them to a desired temperature to perform the reaction; or a method of charging dropwise the fluoro compound at a desired temperature to react them; a method of simultaneously adding desired molar ratio of the fuming sulfuric acid and the fluoro compound to react them and a method of adding dropwise the fuming sulfuric acid into the fluoro compound. Thus, the reaction is smoothly and advantageously performed.

The reaction time is usually in a range of about 1 to 20 hours preferably 2 to 10 hours.

The invention will be further illustrated by certain specific examples which are included for purposes of illustration only and are not intended to be limiting unless otherwise specified.

EXAMPLE 1

In a three necked flask equipped with a stirrer, a dropping funnel and a reflux condenser, 2600 g (9.75 moles as $SO_3$) of fuming sulfuric acid containing 30% of $SO_3$ was charged and was heated at 90° C and then, 524 g (1.56 moles) of methyl-4-iodoperfluoro-n-butyrate having the formula $I(CF_2)_3CO_2CH_3$ was added dropwise to it with stirring under maintaining the temperature at 85° to 95° C in 3 hours.

The gaseous reaction mixture was passed through a gas washing bottle containing a concentrated sulfuric acid and was collected in a flask cooled with a dry-ice-ethanol coolant.

The collected reaction product comprises $SO_2$ and perfluoro-γ-butyrolactone having the formula

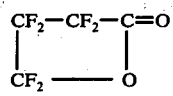

According to on distillation, 236 g (yield of 78%) of perfluoro-γ-butyrolactone having a boiling point of 17° to 19° C was separated.

NMR analysis confirmed that perfluorodicarboxylic fluoride was not included.

EXAMPLE 2

In a three necked flask equipped with a stirrer, a dropping funnel and a reflux condenser, 575 g (2.16 moles as $SO_3$) of fuming sulfuric acid containing 30% of $SO_3$ was charged and then, 82.4 g (0.254 mole) of 4-iodoperfluoro-n-butyryl fluoride having the formula $I(CF_2)_3COF$ was added dropwise to it with stirring under maintaining the reaction temperature at 80° to 90° C in 1 hour.

In accordance with the process of Example 1, $SO_2$ was separated from the gaseous mixture and the analysis was carried out.

The reaction mixture included $SO_2$ and perfluoro-γ-butyrolactone without perfluorodicarboxylic fluoride. According to on distillation, 37.5 g (yield of 76 mole %) of perfluoro-γ-butyrolactone was separated.

EXAMPLE 3

In a three necked flask equipped with a stirrer, a dropping funnel and a reflux condenser, 500 g (1.88 moles as $SO_3$) of fuming sulfuric acid containing 30% of $SO_3$ was charged and then, 120 g (0.344 mole) of N-ethyl-4-iodoperfluoro-n-butylamide was added dropwise to it with stirring under maintaining the reaction temperature at 80° to 90° C in 2 hours. In accordance with the process of Example 1, the reaction product was separated to obtain 48.8 g (yield of 73%) of perfluoro-γ-butyrolactone.

EXAMPLE 4

In a three necked flask equipped with a stirrer, a dropping funnel and a reflux condenser, 500 g (1.88 moles as $SO_3$) of fuming sulfuric acid containing 30% of $SO_3$ was charged and then, 142 g (0.38 mole) of 5-iodoperfluoro-n-valeryl fluoride was added dropwise to it with stirring under maintaining the reaction temperature at 90° to 105° C in 2 hours.

In accordance with the process of Example 1, the reaction product was separated to obtain 69.5 g (yield of 75%) of perfluoro-δ-valerolactone having a boiling point of 38° to 40° C.

No perfluorodicarboxylic fluoride was incorporated.

What is claimed is:

1. A process for producing perfluorolactone having the formula

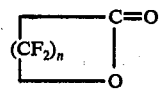

wherein n is an integer of 2 to 4, which comprises reacting a fluoro compound having the formula

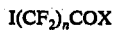

wherein $n$ is an integer of 2 to 4 and X represents a halogen atom, —OR or —NR$^1$R$^2$, and R, R$^1$ and R$^2$ respectively represent hydrogen atom or a C$_1$- C$_{10}$ alkyl group, with fuming sulfuric acid at a temperature in the range of 30° to 150° C.

2. A process according to claim 1, wherein the fluoro compound has the formula

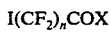
I(CF$_2$)$_n$COX wherein $n$ is an integer of 2 to 4, and X represents a halogen atom or —OR or —NR$^1$R$^2$ and R, R$^1$ and R$^2$ respectively represent hydrogen atom or a C$_1$- C$_3$ alkyl group.

3. A process according to claim 1, wherein the concentration of SO$_3$ in the fuming sulfuric acid is in a range of 5 to 95% by weight.

4. A process according to claim 1, wherein the concentration of SO$_3$ in the fuming sulfuric acid is in a range of 20 to 60% by weight.

5. A process according to claim 1, wherein excess of the fuming sulfuric acid of more than 2 moles as the concentration of SO$_3$ is used per 1 mole of the fluoro compound.

6. A process according to claim 1, wherein a catalyst of mercuric sulfate, cadmium sulfate or zinc sulfate is used in the reaction.

7. A process according to claim 6, wherein chlorine gas is added in the reaction.

8. A process for producing perfluoro butyrolactone having the formula:

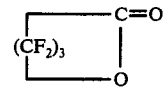

which comprises reacting a compound of the formula I(CF$_2$)$_3$COX wherein X represents a halogen atom, —OR or —NR'R$^2$, wherein R, R' and R$^2$ respectively represent a member selected from the group consisting of hydrogen and C$_1$-C$_{10}$ alkyl, with fuming sulfuric acid at a temperature in the range of 30° to 150° C.

9. A process for producing perfluorovalero lactones having the formula:

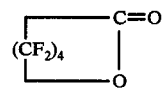

which comprises reacting a fluoro compound of the formula I(CF$_2$)$_4$COX wherein X represents a halogen atom, —OR, or —NR'R$^2$, wherein R$_1$R' and R$^2$ respectively represent a member selected from the group consisting of hydrogen and C$_1$-C$_{10}$ alkyl, with fuming sulfuric acid at a temperature of the range of 30° to 150° C.

* * * * *